US00PP29239P3

(12) United States Plant Patent
Probasco et al.

(10) Patent No.: US PP29,239 P3
(45) Date of Patent: Apr. 17, 2018

(54) HOP PLANT NAMED 'HBC 566'

(50) Latin Name: *Humulus lupulus*
Varietal Denomination: HBC 566

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 14/756,966

(22) Filed: Nov. 2, 2015

(65) Prior Publication Data

US 2016/0360661 P1 Dec. 8, 2016

Related U.S. Application Data

(60) Provisional application No. 62/230,414, filed on Jun. 4, 2015.

(51) Int. Cl.
*A01H 5/00* (2006.01)

(52) U.S. Cl.
USPC ..... Plt./236

(58) Field of Classification Search
USPC ..... Plt./236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 566' is disclosed. The cones of 'HBC 566' mature in September. 'HBC 566' is used for its aromatic quality.

4 Drawing Sheets

Genus and species: *Humulus lupulus*.
Variety denomination: 'HBC 566'.

STATEMENT REGARDING FEDERALLY SPONSORED RESEARCH OR DEVELOPMENT

None

BACKGROUND OF THE INVENTION

'HBC 566' is a product of a controlled breeding program carried out by the inventors in the Yakima Valley of Washington State. 'HBC 566' resulted from the cross pollination of 'YCR 21' (unpatented *Humulus lupulus* female plant) and male plant '01239-2' (unpatented). The cross pollination was made in 2007. The plant was selected and assigned accession number 566 in 2010. At this time, it was asexually reproduced via softwood cuttings in a greenhouse near Toppenish, Wash. Prior to 2014, the original single plant of 'HBC 566' was expanded to multiple plants, which were planted in the area of Toppenish, Wash. By 2014, the plants had been observed and evaluated for several years. Throughout several generations of asexual propagation, 'HBC 566' has been observed to retain its distinctive characteristics and remain true to type.

COMPARISON OF 'HBC 566' TO PARENT PLANT AND COMPARISON CULTIVAR

Table 1. below, sets forth some of the distinguishing characteristics of 'HBC 566' as compared to its female parent 'YCR 21', and to the 'Cascade' cultivar as a closely comparable cultivar.

TABLE 1

| | Instant Plant | Mother Plant | Cascade |
|---|---|---|---|
| ID #: | 'HBC 566' | 'YCR 21' | — |
| UV Alpha: | 7.5-9.5% | 12.5-16% | 5.5-9.0% |
| UV Beta: | 2.5-3.5% | 3.8-4.7% | 6.0-7.5% |
| Alpha:Beta: | 3.0 | 3.4 | 1.1 |
| % Co—H: | 20-25% | 33.5-37% | 30-35% |
| Matures: | <Sep. 7 | Sep. 7-Sep. 21 | Sep. 5-Sep. 15 |

BRIEF DESCRIPTION OF THE PHOTOGRAPHS

Figure 1:
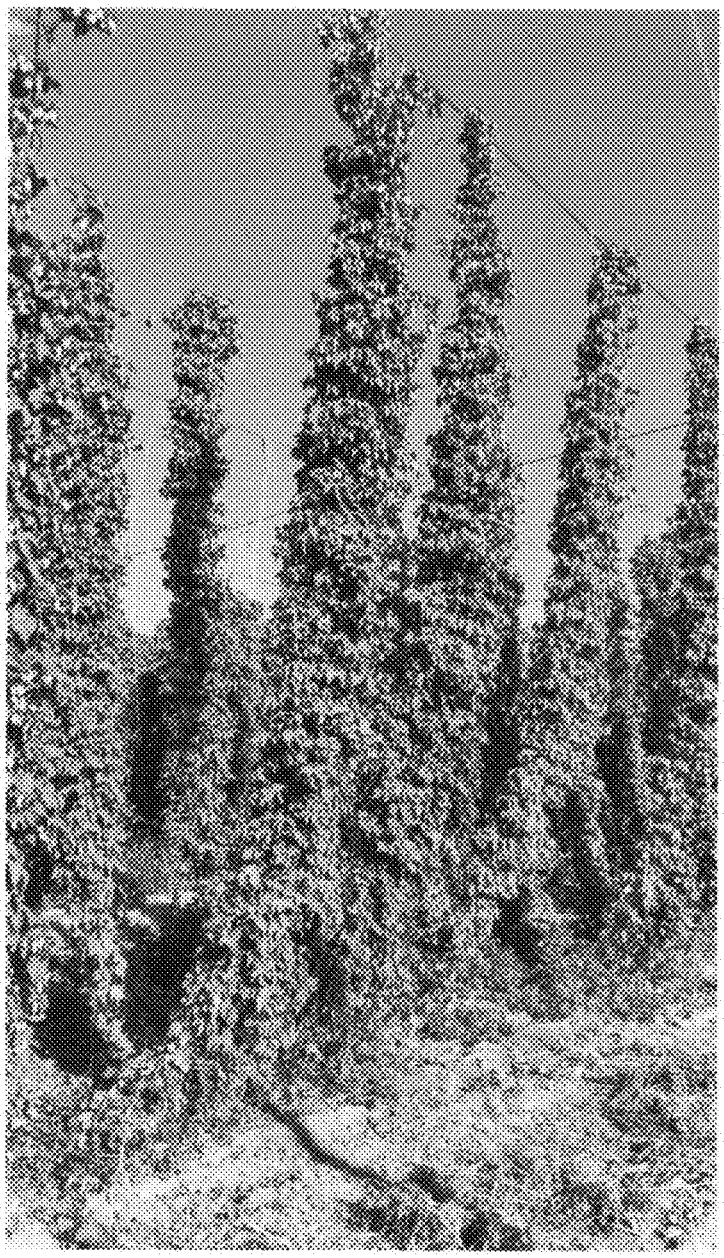
FIG. 1 illustrates a mature 'HBC 566' hop plant grown on a trellis.
Figure 2:
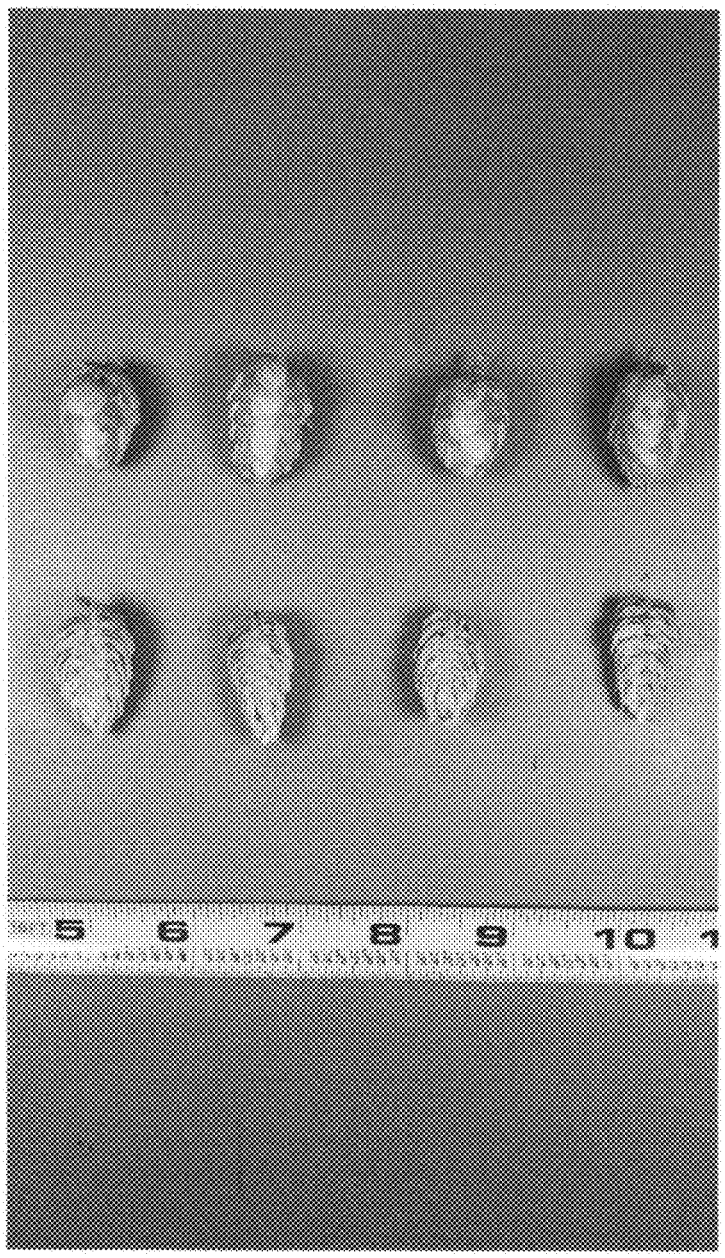
FIG. 2 illustrates whole cones and cross sections of cones of the 'HBC 566' hop plant.
Figure 3:
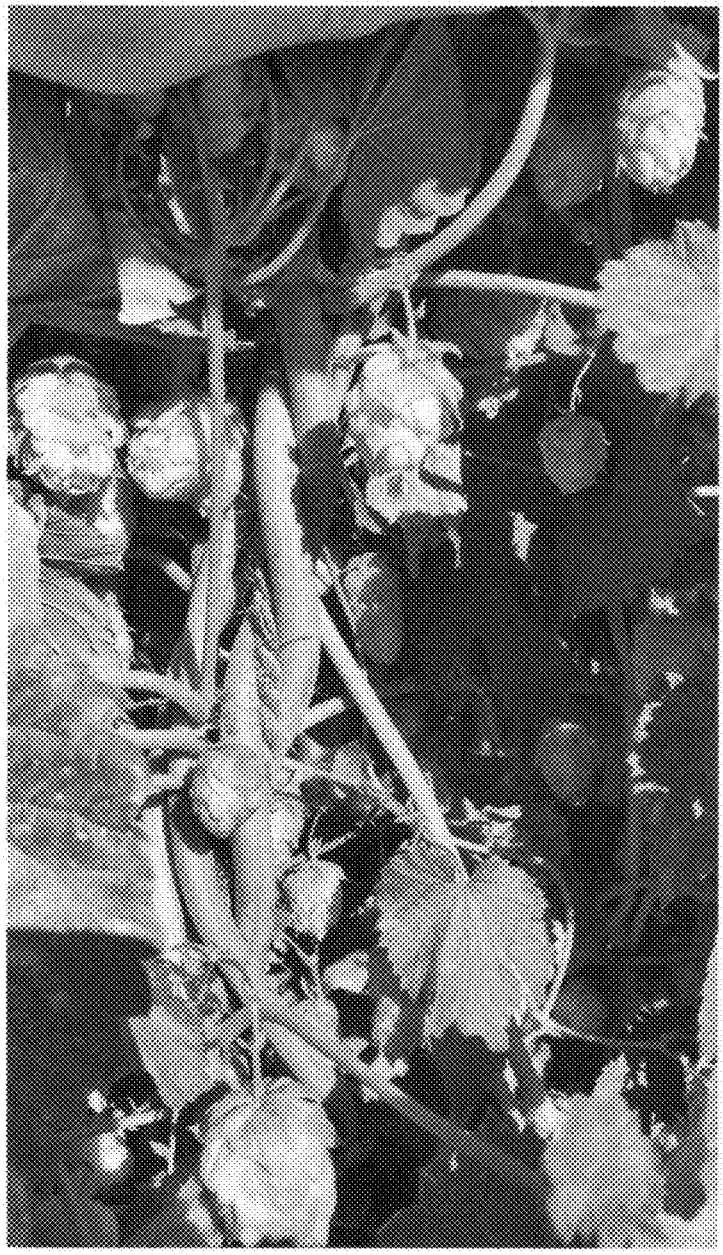
FIG. 3 illustrates the bine of a mature 'HBC 566' hop plant.
Figure 4:
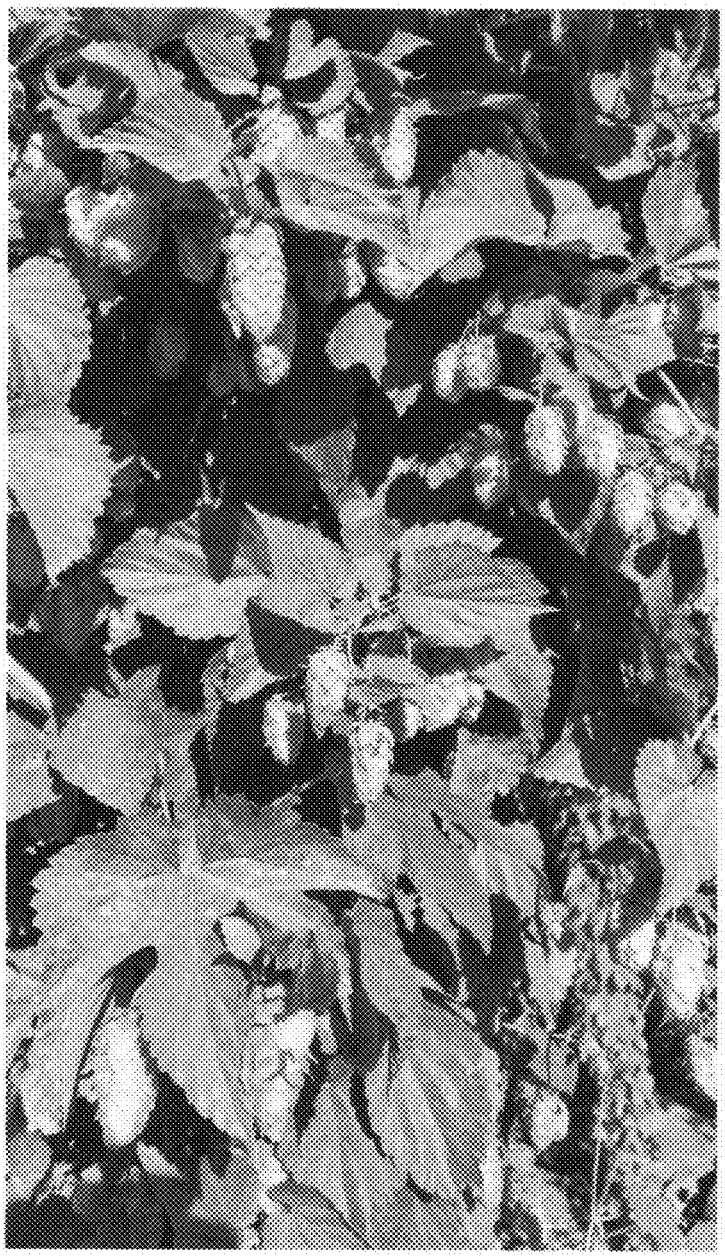
FIG. 4 illustrates the cones and leaves of a mature 'HBC 566' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013-2014 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Use: Brewing.

Harvest date: September (during 2013 to 2014 growing seasons at Toppenish, Wash.).

Ploidy: Diploid, 2n=2x.

Disease susceptibility: Moderate resistance to powdery mildew and susceptible to downy mildew.

Crop yield: 1400 lbs per acre.

Plant shape: Climbing bine, columnar growth.

Bine:

*Color*.—Yellow Green 146C.
*Stipule direction*.—Horizontal.
*Stipule color*.—Yellow Green 144A.
*Average number per bine*.—Two per node.
*Stripe present*.—Yes.
*Stripe color*.—Yellow Green 146B.
*Bine diameter*.—7.5 mm at base and 10.0 mm at nine feet.
*Bine length*.—Grown on an 18 ft trellis, typical growth 18-25 ft.
*Lateral length between internodes*.—200-210 mm on average.
*Lateral length*.—60 cm-150 cm.
*Lateral diameter*.—2-4 mm at the base and 0.5-1 mm at the terminus.
*Lateral color*.—144B.

Leaf:

*Arrangement*.—Opposite.
*Shape*.—Cordate and palmate.
*Apex*.—Acuminate.
*Base*.—Cordate.
*Average leaf length*.—14.1 cm.
*Average leaf width*.—13.4 cm.
*Color of mature leaf upper surface*.—Yellow Green 147A.
*Color of mature leaf lower surface*.—Yellow Green 147B.
*Color of immature leaf upper surface*.—Yellow Green 147A.
*Color of immature leaf lower surface*.—Yellow Green 147B.
*Number of lobes*.—1-7.
*Margin*.—Serrate.
*Serrations per inch*.—5-10.
*Petiole length*.—10 cm.
*Petiole diameter*.—3-4 mm at the base.
*Petiole color* (*base*).—Yellow Green 146B.

Cone:

*Weight*.—800-1000 mg.
*Shape*.—Oval.
*Length*.—40 mm.
*Diameter*.—23 mm.
*Pickability*.—Good pickability.
*Bract shape*.—Orbicular.
*Bract apex*.—Acuminate.
*Bract margin*.—Entire.
*Bract base*.—Rounded.
*Bract color upper*.—Yellow Green 146D.
*Bract color lower*.—Yellow Green 149D.
*Bracteole shape*.—Ovate.
*Bracteole length*.—4-5 mm.
*Bracteole width*.—3-4 mm.
*Bracteole color upper*.—Yellow Green 145B.
*Bracteole color lower*.—Yellow Green 145B.
*Lupulin gland number per cone*.—Moderate.
*Lupulin gland color*.—Yellow 14B.

Analytical characteristics:

*Alpha acid* (*as % of cone weight*).—8.0-9.6%.
*Beta acid* (*as % of cone weight*).—2.2-2.9%.
*Cohumulone* (*as % of alpha acids*).—21-23%.
*Total oil*.—1.3-1.7 mL per 100 g hops.
*Myrcene*.—36-55.6%.
*Humulene*.—10.1-15.1%.
*Caryophyllene*.—8.1-11.6%.
*Farnesene*.—0.03-0.76%.
*Linalool*.—0.68-0.79%.
*Storage stability*.—60-70% alpha acids remaining after 6 months storage at room temperature.

The invention claimed is:

1. A new and distinct Hop plant as illustrated and described herein.

* * * * *